United States Patent
Maiti et al.

[11] Patent Number: 5,888,998
[45] Date of Patent: Mar. 30, 1999

[54] 2-OXO-1-AZETIDINE SULFONIC ACID DERIVATIVES AS POTENT β-LACTAMASE INHIBITORS

[75] Inventors: Samarendra N. Maiti; Eduardo L. Setti; Oludotun A. Phillips; Andhe V. Narender Reddy, all of Edmonton; Ronald G. Micetich, Sherwood Park; Rajeshwar Singh, Edmonton, all of Canada; Fusahiro Higashitani, Tokushima, Japan; Chieko Kunugita; Koichi Nishida, both of Itano-gun, Japan; Tatsuya Uji, Tokushima, Japan

[73] Assignees: Synphar Laboratories, Inc., Alberta, Canada; Taiho Pharmaceutical Co., Ltd., Hanno Saitama, Japan

[21] Appl. No.: 840,608

[22] Filed: Apr. 24, 1997

[51] Int. Cl.$^6$ ............... C07D 205/085; A61K 31/395
[52] U.S. Cl. ........................... 514/210; 540/355
[58] Field of Search ................ 514/210; 540/355

[56] References Cited

U.S. PATENT DOCUMENTS

| | | | |
|---|---|---|---|
| 4,632,985 | 12/1986 | Kronenthal | 540/355 |
| 4,775,670 | 10/1988 | Sykes et al. | 514/210 |
| 5,112,968 | 5/1992 | Treuner | 540/355 |

OTHER PUBLICATIONS

Neil S. Isaacs et al., "The Inhibition of Bacterial β–Lactamases by Some Monocyclic β–Lactams", *The Journal of Antibiotics*, 35(5), 589, 1982.

Karen Bush, et al, "Interaction of Azthreonam and Related Monobactams with β–Lactamases from Gram–Negative Bacteria", *Antimicrobial Agents and Chemotherapy*, 22(3), 414, 1982.

R.L. Then, "Interaction of Ro 17–2301 (AMA–1080) with β–Lactamases", Chemotherapy (Basel), 30, 398, 1984.

Yuko Sakura et al, "Characteristics of Aztroenonam as a Substrate, Inhibitor and Inducer for β–Lactamases", *The Journal of Antibiotics*, 43 )4), 403, 1990.

*Primary Examiner*—Mark L. Berch
*Attorney, Agent, or Firm*—Nikaido Marmelstein Murray & Oram, LLP

[57] ABSTRACT

A compound of formula (I)

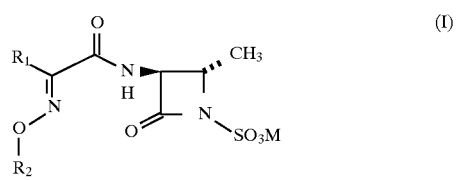

wherein $R_1$ is selected from the group consisting of 2-thienyl, 2-furyl, 2-pyrrolyl, 1-methyl-2-pyrrolyl, 2-amino-1-thiazolyl and 5-isothiazolyl;

$R_2$ is selected from the group consisting of:

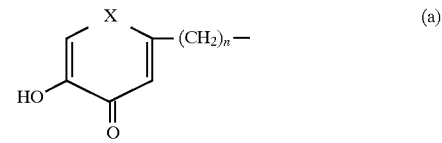

(a)

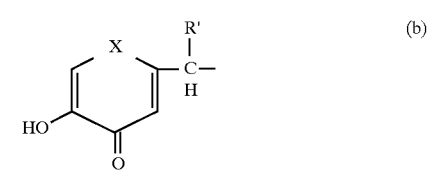

(b)

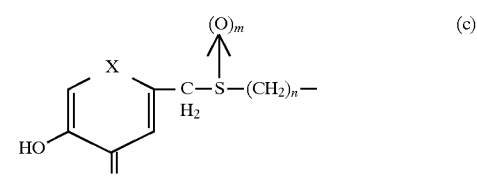

(c)

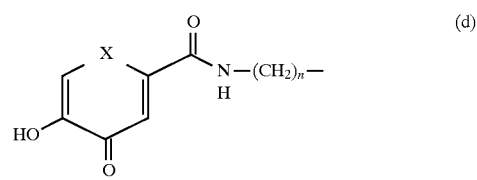

(d)

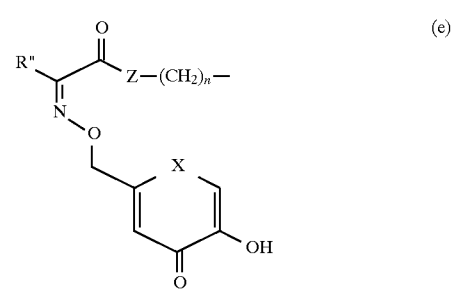

(e)

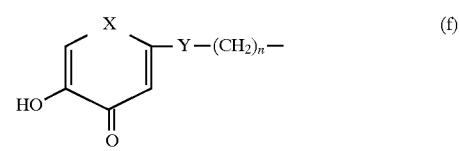

(f)

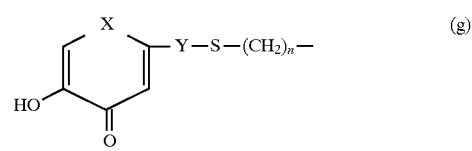

(g)

and M is hydrogen or a pharmaceutically acceptable cation;

wherein the oxyimino fragment (=N—OR$_2$) in formula (I) is in the 'anti' orientation.

11 Claims, No Drawings

2-OXO-1-AZETIDINE SULFONIC ACID DERIVATIVES AS POTENT β-LACTAMASE INHIBITORS

BACKGROUND OF THE INVENTION

This invention relates to novel 2-oxo-1-azetidine sulfonic acid derivatives which are of value for use in combination with β-lactam antibiotics to increase their effectiveness in infection caused by β-lactamase producing bacteria.

Of the commercially available β-lactam antibiotics, penicillins and cephalosporins are best known and frequently used. Although widely used as useful chemotherapeutic agents, enzymatic inactivation of β-lactam antimicrobial agents has been an obstacle to the treatment of infection for as long as these agents have been used. The production of enzymes that degrade the β-lactam containing antimicrobial agents—penicillins and cephalosporins—is an important mechanism of bacterial resistance, thereby causing the antibiotic to lose it's antimicrobial activity. A novel approach to countering these bacterial enzymes is the delivery of a β-lactam antimicrobial agent together with an enzyme inhibitor. When a β-lactamase inhibitor is used in combination with a β-lactam antibiotic, it can increase or enhance the antibacterial effectiveness of the antibiotic against certain microorganisms.

The present invention provides certain novel 2-oxo-1-azetidine sulfonic acid derivatives which are potent inhibitors of bacterial β-lactamases, particularly against class C β-lactamases (cephalosporinase). Aztreonam (U.S. Pat. No. 4,775,670) is a known monobactam antibiotic. Several publications [(e.g., Antimicrobial Agents of Chemotherapy, vol. 22, pp. 414–420, 1982; Chemotherapy, vol. 30, pp. 398–407 (1984); J. Antibiotics, vol. 35, no. 5, pp. 589–593 (1982); J. Antibiotics, vol. 43, no. 4, pp. 403–410 (1990)] suggest that aztreonam possesses β-lactamase inhibitory properties.

SUMMARY OF THE INVENTION

It is an object of the present invention to provide novel and new 2-oxo-1-azetidine sulfonic acid derivatives having β-lactamase inhibitory activity, particularly against class C β-lactamases (cephalosporinase).

It is a further object of the invention to provide pharmaceutical compositions comprising a β-lactamase inhibitor of this invention in combination with a β-lactam antibiotic and a pharmaceutically acceptable carrier or diluent.

It is an additional object of the invention to provide an improved method for the treatment of bacterial infections caused by class C β-lactamase (cephalosporinase) producing bacteria in mammalian subjects, particularly in human.

Accordingly, this invention provides novel 2-oxo-1-azetidinesulfonic acid derivatives having the formula (I):

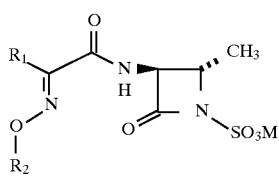

(I)

and the pharmaceutically acceptable salts thereof,
  wherein $R_1$ is a 5-membered heterocyclic ring and $R_2$ is selected from any one of the following groups:

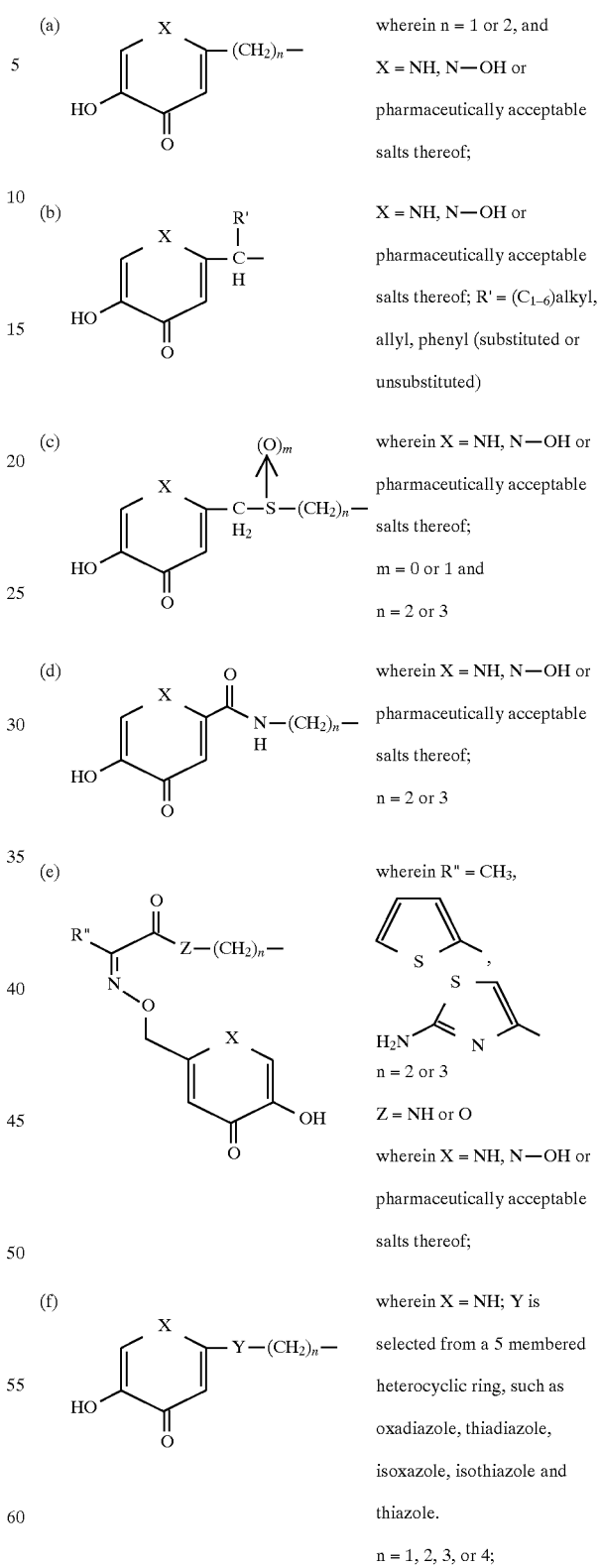

(g) 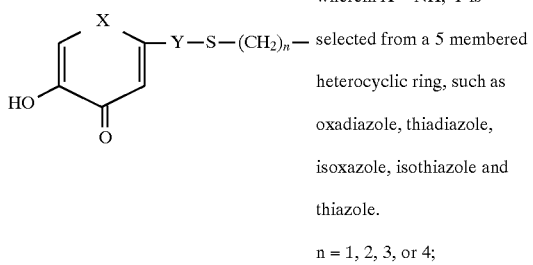 wherein X = NH; Y is selected from a 5 membered heterocyclic ring, such as oxadiazole, thiadiazole, isoxazole, isothiazole and thiazole.

n = 1, 2, 3, or 4;

M is hydrogen or a pharmaceutically acceptable salt forming cation.

The present inventors found that the oxyimino group, i.e. =N—OR$_2$ in the formula (I) while in the 'anti' orinentation provides excellent synergy with a β-lactam antibiotic against class C β-lactamase (cephalosporinase) producing microorganisms. In particular, they show markedly superior synergy in combination with cephalosporins (e.g., ceftazidime) against *Pseudomonas aeruginosa*.

The present inventors also found that the inhibitory activity against isolated β-lactamase (e.g., cephalosporinase from *P. aeruginosa* 46012) and the synergy with a β-lactam antibiotic e.g., ceftazidime is greatly influenced by the nature of the heterocyclic ring represented by R$_1$ and the nature of the substituent in the oxime fragment represented by R$_2$.

Thus, thiophene is the preferred 5-membered heterocyclic ring as R$_1$ and hydroxy pyridone including N-hydroxy pyridone is the preferred 6-membered heterocyclic ring [attached through a spacer to the oxygen atom; items (a) to (g)] as one of the components represented by R$_2$.

DETAILED DESCRIPTION OF THE INVENTION

The β-lactamase inhibitors of this invention are the compounds having the formula (I)

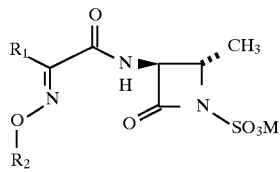 (I)

The present β-lactamase inhibitors of the invention are effective in enhancing the antimicrobial activity of β-lactam antibiotics, when used in combination to treat a mammalian subject suffering from a bacterial infection caused by a β-lactamase producing microorganism. Examples of antibiotics which can be used in combination with the compounds of the present invention are commonly used penicillins such as amoxicillin, ampicillin, azlocillin, mezlocillin, apalcillin, hetacillin, bacampicillin, carbenicillin, sulbenicillin, ticarcillin, piperacillin, mecillinam, pivmecillinam, methicillin, ciclacillin, talampicillin, aspoxicillin, oxacillin, cloxacillin, dicloxacillin, flucloxacillin, nafcillin, pivampicillin; commonly used cephalosporins such as cephalothin, cephaloridine, cefaclor, cefadroxil, cefamandole, cefazolin, cephalexin, cephradine, ceftizoxime, cefoxitin, cephacetrile, cefotiam, cefotaxime, cefsulodin, cefoperazone, ceftizoxime, cefmenoxime, cefmetazole, cephaloglycin, cefonicid, cefodizime, cefpirome, ceftazidime, ceftriaxone, cefpiramide, cefbuperazone, cefozopran, cefepime, cefoselis, cefluprenam, cefuzonam, cefpimizole, cefclidin, cefixime, ceftibuten, cefdinir, cefpodoxime proxetil cefteram pivoxil, cefetamet pivoxil, cefcapene pivoxil, cefditoren pivoxil; commonly used carbapenem antibiotics such as imipenem, meropenem, biapenem, panipenem and the like; commonly used monobactams such as aztreonam and carumonam and salts thereof.

Furthemore, the β-lactamase inhibitors of the present invention can be used in combination with another β-lactamase inhibitor to enhance the antimicrobial activity of any of the above mentioned β-lactam antibiotics. For example, the inhibitors of this invention can be combined with piperacillin/tazobactam combination; ampicillin/sulbactam combination; amoxycillin/clavulanic acid combination; ticarcillin/clavulanic acid combination, cefoperazone/sulbactam combination, and the like.

R$_1$ in the formula (I) is a 5-membered heterocyclic ring containing from 1 to 4 heteroatoms independently selected from the group consisting of O, S and N.

Preferred heterocyclic rings are:

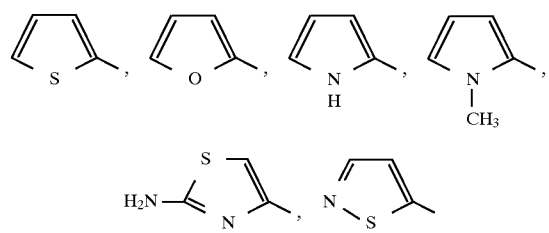

Preferably, R$_1$ in the formula (I) is thiophene and 2-aminothiazole;

Even more preferably R$_1$ is thiophene.

R$_2$ in the formula (I) is selected from any one of the following groups:

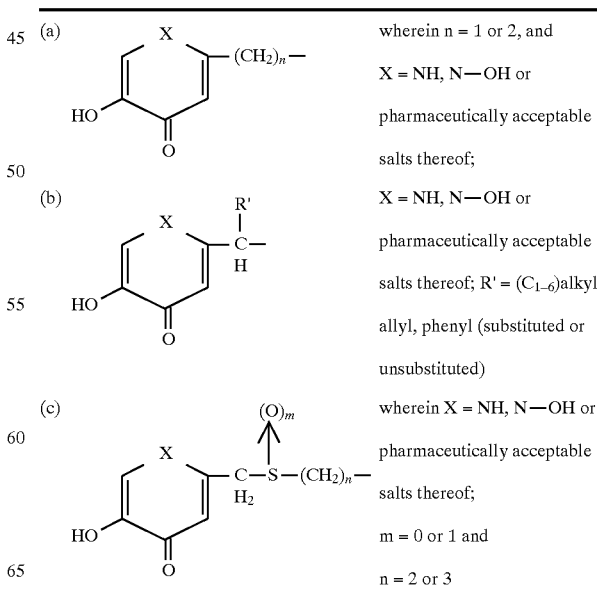

(a) wherein n = 1 or 2, and

X = NH, N—OH or pharmaceutically acceptable salts thereof;

(b) X = NH, N—OH or pharmaceutically acceptable salts thereof; R' = (C$_{1-6}$)alkyl, allyl, phenyl (substituted or unsubstituted)

(c) wherein X = NH, N—OH or pharmaceutically acceptable salts thereof;

m = 0 or 1 and n = 2 or 3

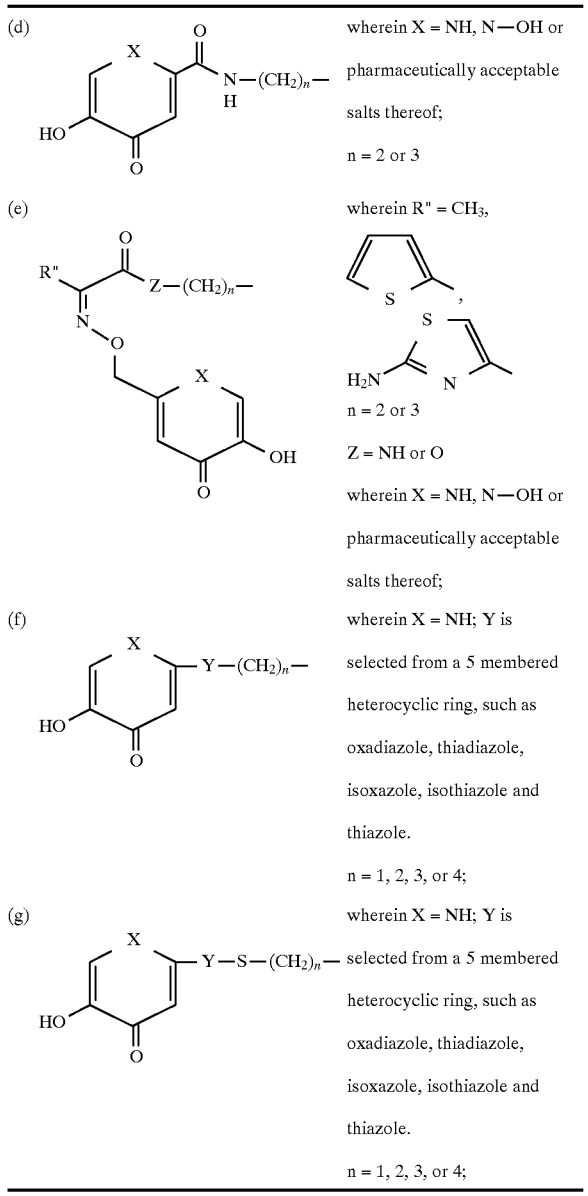

Examples of 5-membered heterocyclic ring represented by "Y" include oxadiazoles, isoxazoles, isothiazoles, thiazoles and thiadiazoles.

Examples of the group for forming a pharmaceutically acceptable salt represented by M in the formula (I) include the inorganic base salts, ammonium salts, organic base salts, basic amino acid salts. Inorganic bases that can form the inorganic base salts include alkali metals (e.g., sodium, potassium, lithium) and alkaline earth metals (e.g., calcium, magnesium); organic bases that can form the organic base salts include cyclohexylamine, benzylamine, octylamine, ethanolamine, diethanolamine, diethylamine, triethylamine, procaine, morpholine, pyrrolidine, piperidine, N-ethylpiperidine, N-methylmorpholine; basic amino acids that can form the basic amino acid salts include lysine, arginine, ornithine and histidine.

As will be appreciated by one skilled in the art, the compounds of formula (I) containing an acidic hydrogen atom other than the $SO_3H$ group at N–1 position are capable of forming salts with basic groups as mentioned earlier. Such salts with pharmaceutically acceptable bases are included in the invention.

Moreover, when M is hydrogen in the formula (I) it can form a zwitterion (inner salt or internal salt) by interacting with a basic nitrogen atom present in the molecule of formula (I).

A variety of protecting groups conventionally used in the β-lactam art to protect the OH groups present in the items (a) to (g) can be used. While it is difficult to determine which hydroxy-protecting group should be used, the major requirement for such a group is that it can be removed without cleaving the β-lactam ring and the protecting group must be sufficiently stable under the reaction conditions to permit easy access to the compound of formula (I). Examples of most commonly used hydroxy-protecting groups are: diphenylmethyl, 4-methoxybenzyl, allyl, etc.

The compounds of this invention having the formula (I) can be prepared using a variety of well known procedures as shown below:

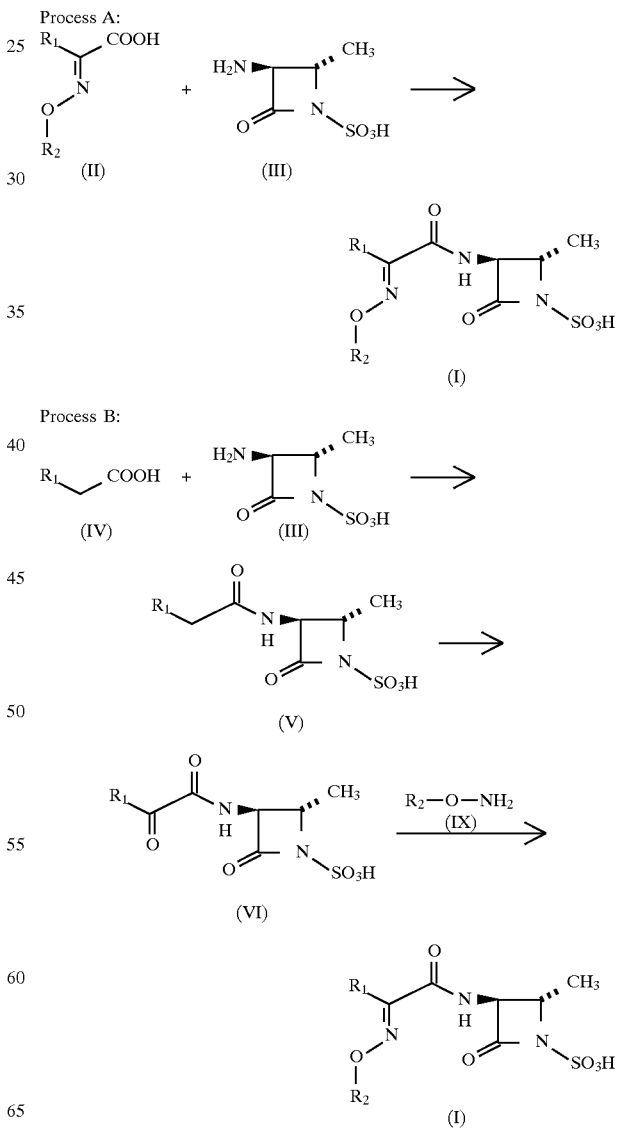

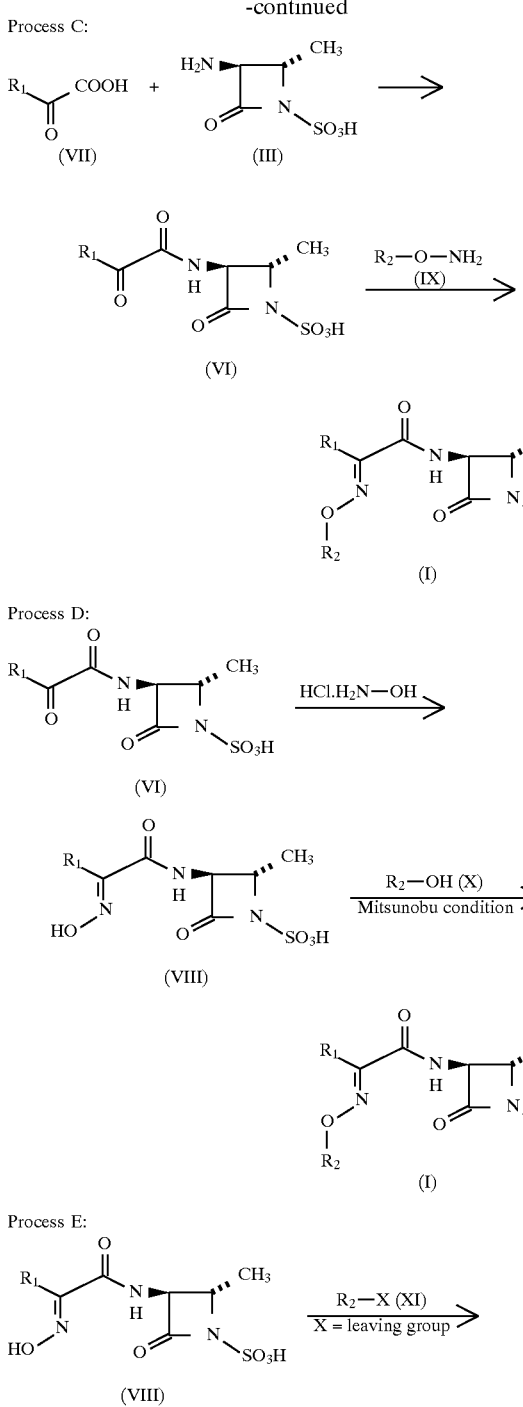

Each procedure utilizes as a starting material the known azetidine of the formula

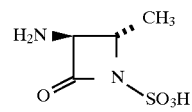

Azetidines of the formula (III) are well known in the literature; see for example the United Kingdom patent application no. 2,071,650 published Sep. 23, 1981; J. Org. Chem., vol. 47, pp. 5160–5167, 1982.

In a preferred procedure the compounds of the formula (I) can be prepared by reacting azetidines of the formula (III) with compounds of the formula

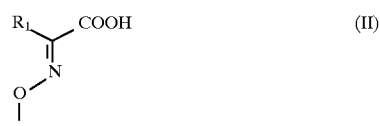

in the presence of a coupling agent. $R_1$ and $R_2$ have the same meaning as described before. It is preferably to first treat the compound of formula III with one equivalent of a base, e.g. tributylamine or trioctylamine or sodium bicarbonate. Preferably the reaction is run in the presence of a substance capable of forming a reactive intermediate in situ, such as N-hydroxybenzotriazole and a catalyst such as dimethylaminopyridine, using a coupling agent such as dicyclohexylcarbodiimide. Exemlpary solvents which can be used for the reaction are dimethylformamide, tetrahydrofuran, dichloromethane or mixtures thereof.

The reaction of an acid of formula (II) or a salt thereof, and a (3S)-3-amino-2-oxo-1-azetidinesulfonic acid salt of formula (III) proceeds most readily if the acid of formula (II) is in activated form. Activated forms of carboxylic acids are well known in the art and include acid halides, acid anhydrides (including mixed acid anhydrides), activated acid amides and activated acid esters.

To be more concrete, such reactive derivatives are:

(a) Acid anhydrides

The acid anhydrides include, among others, mixed anhydride with a hydrohaloic acid e.g. hydrochloric acid, hydrobromic acid; mixed anhydrides with a monoalkyl carbonic acid; mixed anhydrides with an aliphatic carboxylic acid, e.g., acetic acid, pivalic acid, valeric acid, isopentanoic acid, trichloroacetic acid; mixed anhydrides with an aromatic carboxylic acid, e.g., benzoic acid; mixed anhydride with a substituted phosphoric acid e.g., dialkoxyphosphoric acid, dibenzyloxyphosphoric acid, diphenoxyphosphoric acid; mixed anhydride with a substituted phosphinic acid e.g., diphenylphosphinic acid, dialkylphosphinic acid; mixed anhydride with sulfurous acid, thiosulfuric acid, sulfuric acid, and the symmetric acid anhydride.

(b) Activated amides

The activated armides include amides with pyrazole, imidazole, 4-substituted imidazoles, dimethylpyrazole, triazole, benzotriazole, tetrazole, etc.

(c) Activated esters

The activated esters include, among others, such esters as methyl, ethyl, methoxymethyl, propargyl, 4-nitrophenyl, 2,4-dinitrophenyl, trichlorophenyl, pentachlorophenyl, mesylphenyl, pyranyl, pyridyl, piperidyl and 8-quinolylthio esters. Additional examples of activated esters are esters with an N-hydroxy compound e.g., N,N-dimethylhydroxylamine, 1-hydroxy-2(1H)pyridone, N-hydroxy succinimide, N-hydroxyphthalimide, 1-hydroxy-1H-benzotriazole, 1-hydroxy-6-chloro-1H-benzotriazole, 1,1'-bis[6-trifluoromethyl)benzotriazolyl]oxalate (BTBO), N-ethoxycarbonyl-2-ethoxy-1,2-dihydroquinoline, and the like.

Appropriate reactive derivatives of organic carboxylic acids are selected from among such ones as mentioned above depending on the type of the acid used. When a free acid is used as the acylating agent, the reaction is preferably carried out in the presence of a condensing agent. Examples of the condensing agent are N,N'-dicyclohexylcarbodiimide, N-cyclohexyl-N'-morpholinoethylcarbodiimide, N-cyclohexyl-N'-(4-diethylaminocyclohexyl) carbodiimide and N-ethyl-N'-(3-dimethylaminopropyl) carbodiimide.

The acylation reaction is usually carried out in a solvent. The solvent includes water, acetone, dioxane, acetonitrile, methylene chloride, chloroform, dichloroethane, tetrahydrofuran, ethyl acetate, dimethylformamide, pyridine and other common organic solvents inert to the reaction.

The acylation reaction can be carried out in the presence of an inorganic base such as sodium hydroxide, sodium carbonate, potassium carbonate or sodium hydrogen carbonate or an organic base such as trimethylamine, triethylamine, tributylamine, N-methylmorpholine, N-methylpiperidine, N,N-dialkylaniline, N,N-dialkylbenzylamine, pyridine, picoline, lutidine, 1,5-diazabicyclo[4.3.0]non-5-ene, 1,4-diazabicyclo[2.2.2]octane, 1,8-diazabicyclo[5.4.4]undecene-7, tetra-n-butylammonium hydroxide. The reaction is usually conducted under cooling or at room temperature.

The amides of formula V, which result from the coupling of acid IV (or a salt thereof) and a (3S)-3-amino-2-oxo-1-azetidinesulfonic acid salt of formula (III) can be oxidized to the corresponding ketoamide of formula VI (Process B). A wide variety of oxidation procedures may be used e.g., potassium nitrosodisulfonate in water (or a mixed aqueous solvent), selenium dioxide in dioxane; use of metal catalysts in the presence of a suitable co-oxidant.

Alternatively, the ketoamide (VI) can be prepared (Process C) by coupling the keto acid (VII) with (3S)-3-amino-2-oxo-1-azetidinesulfonic acid of formula III (or a salt thereof).

The compounds of this invention of formula (I) can also be prepared by reacting a ketoamide (VI) (Process B or Process C) having the formula

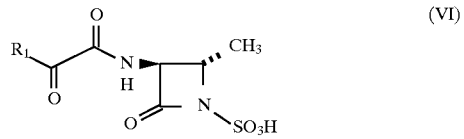
(VI)

with a hydroxylamine derivative (or a salt thereof) of formula

R$_2$—O—NH$_2$ (IX)

wherein R$_1$ and R$_2$ have the same meaning as described before.

Alternatively, the ketoamide (VI) can be reacted with hydroxylamine hydrochloride to provide the hydroxyimino derivative (VIII) (Process D). Coupling of the hydroxyimino derivative of formula (VIII).

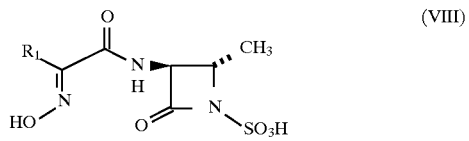
(VIII)

with the alcohol (R$_2$—OH, X) under Mitsunobu conditions (PPh$_3$/DEAD/THF) will provide the compounds of formula (I). R$_2$ has the same meaning as described before.

Alternatively, the compounds of formula (I) can be prepared by reacting the hydroxyimino derivative (VIII) (Process E) with a compound of the formula, R$_2$—X (XI) wherein X is a leaving group such as halogen, trifluoroacetate, alkylsulfonate, arylsulfonate or other activated esters of alcohols.

Wherein R$_2$ has hereinbefore been defined.

The compounds of formula (I) which has a sulfo group (SO$_3$H) at N–1 position can generally react with a base to form a salt thereof. Therefore, the compound (I) may be recovered in the form of a salt and such salt may be converted into the free form or to another salt. And, the compound (I) obtained in the free form may be converted into a salt.

The present invention also covers the compound (I) in a pharmaceutically acceptable salt form. For conversion of the compound obtained in the salt form into the free form, the method using an acid can be used. Usable acids depend on the kind of protective group and other factors. The acids include, for example, hydrochloric acid, sulfuric acid, phosphoric acid, formic acid, acetic acid, trifluoroacetic acid, p-toluenesulfonic acid, among others. Acid ion exchange resins can also be used. Solvents may be used include hydrophilic organic solvents such as acetone, tetrahydrofuran, methanol, ethanol, acetonitrile, dioxane, dimethylformamide, dimethyl sulfoxide, water and mixed solvents thereof.

Compounds of formula (II) are novel compounds and as such form an integral part of this invention. The compounds of formula (II) can be prepared by reacting an intermediate of formula (XII).

(XII)

With the alcohol R$_2$—OH (X) under standard Mitsunobu conditions (PPh$_3$/DEAD/THF; D. L. Hughes, The Mitsunobu Reactions in Organic Reactions; P. Beak et al., Eds.; John Wiley & Sons, Inc.: New York, vol. 42, pp. 335–656, 1992).

R$_1$ has the same definition as defined before. R$_3$ is a protective group for the carboxyl group. The protective groups for said carboxyl group include all groups generally usable as carboxyl-protecting groups in the field of β-lactam compound and organic chemistry, for example, methyl, ethyl, propyl, isopropyl, allyl, t-butyl, benzyl, p-methoxybenzyl, p-nitrobenzyl, benzhydryl, methoxymethyl, ethoxymethyl, acetoxymethyl, pivaloyloxymethyl, trityl, 2,2,2-trichloroethyl, β-iodoethyl, t-butyldimethylsilyl, dimethylsilyl, acetylmethyl, among others.

The selection of the said protective group should be in such a way which at the end of the above described reaction sequence can be cleaved from the carboxyl group under conditions that do not alter the rest of the molecule. Preferred protective groups are methyl, ethyl, allyl.

The removal of protective groups R$_3$ can be effected by selective application of a per se known method such as the method involving the use of an acid, one using a base, the method involving the use of palladium tetrakis. The method involving the use of an acid employs according to the type of protective group and other conditions, inorganic acid such as hydrochloric acid, phosphoric-acid; organic acid like formic acid, acetic acid, trifluoroacetic acid, acidic ion exchange resins and so on. The method involving the use of a base employs, according to the type of protective group and other conditions, inorganic bases such as the hydroxides or carbonates of alkali metals (e.g., sodium, potassium etc.) or of alkaline earth metals (e.g., calcium, magnesium, etc.) or organic bases such as metal alkoxides, organic amines, quarternary ammonium salts or basic ion exchange resins, etc.

The reaction temperature is about 0° to 80° C., more preferably about 10° to 40° C. The reaction is usually carried out in a solvent. As the solvent, organic solvents such as ethers (e.g., dioxane, tetrahydrofuran, diethyl ether), esters (e.g., ethyl acetate, ethyl formate), halogenated hydrocarbons (e.g., chloroform, methylene chloride), hydrocarbons (e.g., benzene, toluene) and amides (e.g. dimethylformamide, dimethylacetamide) and a mixture thereof are used.

Alternatively, the intermediate of formula (II) can be prepared by reacting the compound of formula (XII) with a compound of formula, $R_2$—X (XI) wherein X is a leaving group such as halogen, trifluoroacetate, alkylsulfonate, arylsulfonate or other activated esters of alcohols.

$R_2$ has the same meaning as defined before.

In another approach, the intermediate (II) can be prepared by reacting a keto acid compound of formula (VII) with a hydroxylamine derivative (or it's salt) of formula, $R_2$—O—$NH_2$ (IX) using conventional procedures; see for example, EP 0251,299 (Kaken); Tokkai Hei 6-263766 (Kyorin, Sep. 20, 1994).

The acids useful for eliminating the hydroxy-protecting group present in the items (a) to (g) in the final step of the preparation of compound of the formula (I) are formic acid, trichloroacetic acid, trifluoroacetic acid, hydrochloric acid, trifluoromethanesulfonic acid or the like. When the acid is used in a liquid state, it can act also as a solvent or an organic solvent can be used as a co-solvent. Useful solvents are not particularly limited as far as they do not adversely affect the reaction. Examples of useful solvents are anisole, trifluoroethanol, dichloromethane and like solvents.

The 2-oxo-1-azetidinesulfonic acid derivatives of the present invention having the formula (I) in which M is hydrogen can be purified by standard procedures well known in the art such as crystallization and chromatography over silica gel or HP-20 column.

The present invention encompasses all the possible stereoisomers as well as their racemic or optically active mixtures.

Typical solvates of the compounds of formula (I) may include water as water of crystallization and water miscible solvents like methanol, ethanol, acetone, dioxane or acetonitrile. Compounds containing variable amounts of water produced by a process such as lyophilization or crystallization from solvents containing water are also included under the scope of this invention.

The β-lactamase inhibitors of this invention of formula (I) are acidic and they will form salts with basic agents. It is necessary to use a pharmaceutically acceptable non-toxic salt. However, when M is hydrogen and when there is an acidic hydrogen in the $R_2$ residue as exemplified by N—OH, the compound of the formula (I) is diacid and can form disalts. In the latter case, the two cationic counterions can be the same or different. Salts of the compounds of formula (I) can be prepared by standard methods known in the β-lactam literature. Typically, this involves contacting the acidic and basic components in the appropriate stoichiometric ratio in an inert solvent system which can be aqueous, non-aqueous or partially aqueous, as appropriate.

Favourable pharmaceutically-acceptable salts of the compounds of formula (I) are sodium, potassium and calcium.

The compounds of the present invention including the pharmaceutically-acceptable salts thereof are inhibitors of bacterial β-lactamases particularly of cephalosporinases (class C enzyme) and they increase the antibacterial effectiveness of β-lactamase susceptible β-lactam antibiotics—that is, they increase the effectiveness of the antibiotic against infections caused by β-lactamase (cephalosporinase) producing microorganisms, e.g. *Pseudomonas aeruginosa*, in particular. This makes the compounds of formula (I) and said pharmaceutically acceptable salts thereof valuable for co-administration with β-lactam antibiotics in the treatment of bacterial infections in mammalian subjects, particularly humans. In the treatment of a bacterial infection, said compound of the formula (I) or salt can be mixed with the β-lactam antibiotic, and the two agents thereby administered simultaneously. Alternatively, the said compound of formula (I) or salt can be administered as a separate agent during a course of treatment with the antibiotic.

The compounds of the invention can be administered by the usual routes. For example, parenterally, e.g. by intravenous injection or infusion, intramuscularly, subcutaneously, orally, intraperitoneally; intravenous injection or infusion being the preferred. The dosage depends on the age, weight and condition of the patient and on the administration route.

The pharmaceutical compositions of the invention may contain a compound of formula (I) or a pharmaceutically acceptable salt thereof, as the active substance mixed with a β-lactam antibiotic in association with one or more pharmaceutically acceptable excipients and/or carriers.

Alternatively, the pharmaceutical compositions of the invention may contain a compound of formula (I) mixed with a β-lactam antibiotic in association with a salt forming basic agent, e.g. $NaHCO_3$ or $Na_2CO_3$ in an appropriate ratio.

The pharmaceutical compositions of the invention are usually prepared following conventional methods and are adminstered in a pharmaceutically suitable form. For instance, solutions for intravenous injection or infusion may contain a carrier, for example, sterile water or, preferably, they may be in the form of sterile aqueous isotonic saline solutions.

Suspensions or solutions for intramuscular injections may contaim, together with the active compound and the antibiotic, a pharmaceutically acceptable carrier, e.g. sterile water, olive oil, ethyl oleate, glycols, e.g. propylene glycol.

For oral mode of administration a compound of this invention can be used in the form of tablets, capsules, granules, powders, lozenges, troches, syrups, elixirs, suspensions and the like, in accordance with the standard pharmaceutical practice. The oral forms may contain together with the active compound of this present invention and a β-lactam antibiotic, diluents, e.g. lactose, dextrose, saccharose, cellulose, cornstarch, and potato starch; lubricants e.g. silica, talc, stearic acid, magnesium or calcium stearate, and/or polyethylene glycols; binding agents e.g. starches, arabic gums, gelatin, methylcellulose, carboxymethyl cellulose, disaggregating agents, e.g. a starch, alginic acid, alginates, sodium starch glycolate, effervescing mixtures; dyestuffs; sweetners; wetting agents e.g., lecithin, polysorbates, laurylsulphates and pharmacologically inactive substances used in pharmaceutical formulations.

As already said, the oxyimino fragment i.e., =N—$OR_2$ in the formula (I) in its 'anti' orientation provides excellent synergy with a β-lactam antibiotic against class C β-lactamase (cephalosporinase) producing microorganisms, *P. aeruginosa*, in particular. Thus this invention includes only those compounds having the formula (I) in which the oxyimino group (=N—$OR_2$) is specifically in the 'anti' orientation as shown in (I). Furthermore, the inhibitory activity against the isolated β-lactamase (e.g., cephalosporinase from P. aeruginosa 46012) and the synergy with a β-lactam antibiotic is greatly influenced by the nature of the heterocyclic ring represented by $R_1$ and the nature of the substituent in the oxime fragment represented by $R_2$.

Thus, thiophene and 2-aminothiazole are the preferred 5-membered heterocyclic rings as $R_1$ and hydroxypyridone including N-hydroxypyridone as represented by

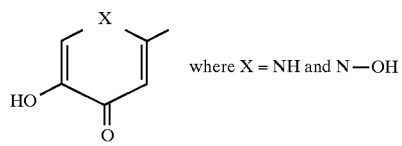

where X = NH and N—OH is the preferred 6-membered heterocyclic ring as one of the components represented by $R_2$. Furthermore, in the above formula when X is N—OH the compounds of formula (I) may have the following keto and enol tautomeric isomers; keto—form being the preferred one.

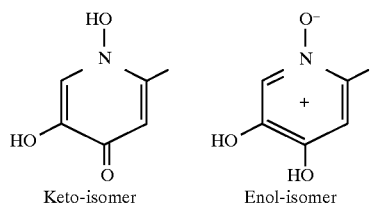

Keto-isomer    Enol-isomer

In most instances, an effective β-lactamase inhibiting dose of a compound of formula (I) or a pharmaceutically acceptable salt thereof, will be a daily dose in the range from about 1 to about 500 mg/kg of body weight orally, and from about 1 to about 500 mg/kg of body weight parenterally. However, in some cases it may be necessary to use dosages outside these ranges. The weight ratio of the β-lactamase inhibitor of the present invention and the β-lactam antibiotic with which it is being administered will normally be in the range of 1:20 to 20:1.

Test for Antibacterial Activity

The compounds of the present invention in combination with ceftazidime were tested for minimal inhibitory concentration (MIC) against the bacteria listed in Table 3, according to the microbroth dilution method described below. The MICs of the antibiotics (ceftazidime) alone, the MICs of ceftazidime in combination with reference compounds particularly aztreonam (ref. compd. I) and the MICs of the β-lactamase inhibitors (10 μg/ml) of the present invention in combination with ceftazidime were determined with the same β-lactamase producing bacteria. After incubation in Mueller-Hinton Broth (Difco) at 37° C. for 18 h, the bacterial suspension was diluted and about $10^5$ CFU/ml was applied to the drug-containing Mueller-Hinton Broth in each well of 96 well plate. The MICs were recorded after 18 h of incubation at 37° C. on the lowest combinations of drug that inhibited visible growth of bacteria.

Test for β-Lactamase Inhibitory Activity

The inhibitory activities of present compounds (β-lactamase inhibitors) against cephalosporinase was measured by spectrophotometric rate assay using 490 nM and using nitrocefin as a substrate (J. Antimicrob. Chemother., vol. 28, pp 775–776, 1991). Table 1 shows the results.

TABLE 1

| Compound | $R_1$ | $R_2$/orientation of $OR_2$ | M | $IC_{50}$, μM |
|---|---|---|---|---|
| Ref. compd. I (Aztreonam) | H₂N-thiazole | HOOC (syn) | H | 0.13 |
| Ref. compd. II | H₂N-thiazole | HOOC (anti) | H | 2.0 |
| Ref. compd. III | thiophene | N-OH hydroxypyridone (syn) | K | 0.04 |
| 1 | thiophene | N-OH hydroxypyridone (anti) | H | 0.06 |

TABLE 1-continued
| Compound | R₁ | R₂/orientation of OR₂ | M | IC$_{50}$, μM |
|---|---|---|---|---|
| 2 | 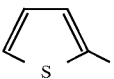 | 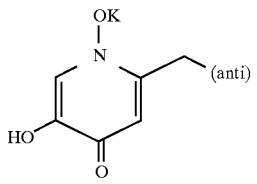 | K | 0.04 |
| 3 | 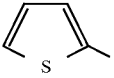 | 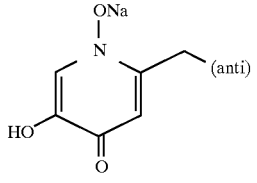 | Na | 0.01 |
| 4 | 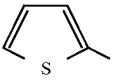 | 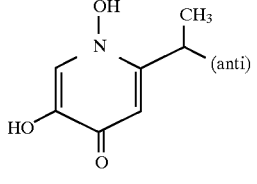 | H | 0.06 |
| 5 | 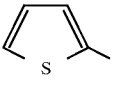 | 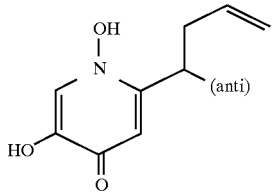 | Na | 0.05 |
| 6 | 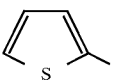 | 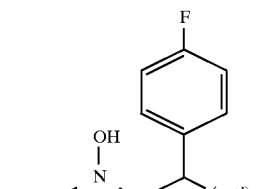 | Na | 0.1 |
| 7 | 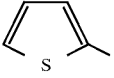 | 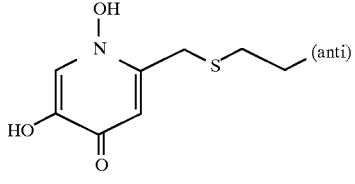 | H | 0.06 |
| 8 | 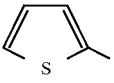 | 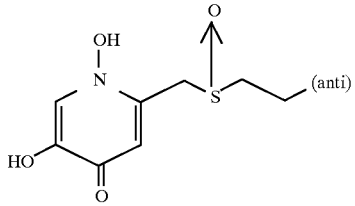 | Na | — |

TABLE 1-continued
| Compound | R₁ | R₂/orientation of OR₂ | M | IC₅₀, μM |
|---|---|---|---|---|
| 9 |  | 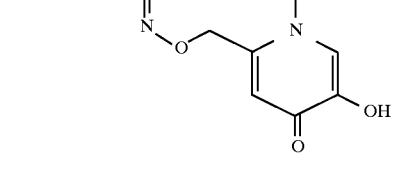 | K | 0.006 |
| 10 |  | 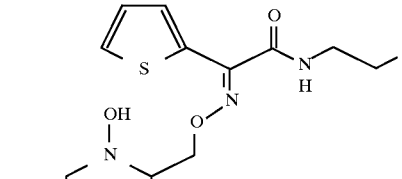 | K | 0.001 |
| 11 |  | 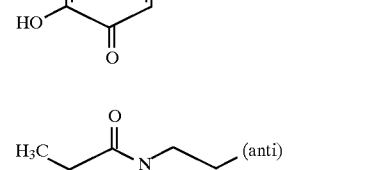 | K | 0.05 |
| 12 |  | 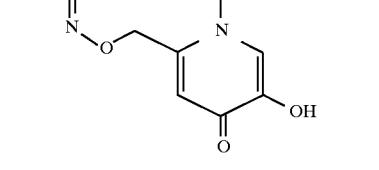 | K | 0.006 |
| 13 |  | 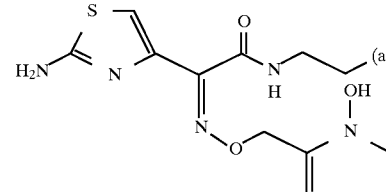 | K | 0.01 |
| 14 |  | 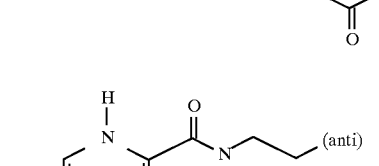 | K | 0.04 |

TABLE 1-continued

| Compound | R₁ | R₂/orientation of OR₂ | M | IC$_{50}$, μM |
|---|---|---|---|---|
| 15 | 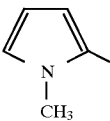 | 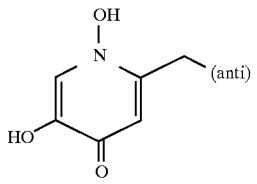 | K | 0.9 |
| 16 | 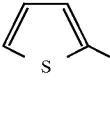 | 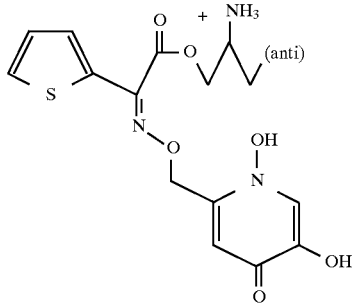 | — | 0.0045 |
| 17 | 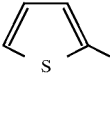 | 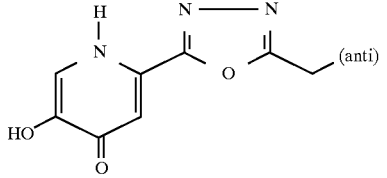 | H | — |
| 18 | 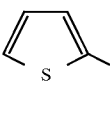 | 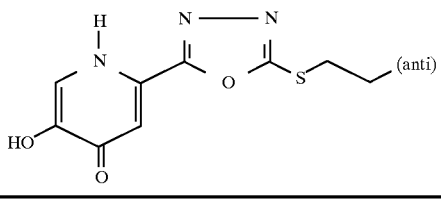 | H | — |

The following examples are provided to demonstrate the operability of the present invention. The structures of the compounds were established by the modes of synthesis and by extensive high field nuclear magnetic resonance spectral techniques.

Preparation of Compound 1

(EXAMPLE 1)

Step 1

Ethyl (E)-2-(2-thienyl)-2-(hydroxyimino) acetate

To a solution of ethyl 2-oxo-2-(2-thienyl) acetate (41 gm, 0.223 moles) in ethanol (350 ml) was added hydroxylamine hydrochloride (23.2 gm, 0.334 moles) followed by pyridine (21.6 ml, 0.267 moles) and the mixture was heated at 40°–45° C. overnight. Solvent was removed under reduced pressure. Ethyl acetate (120 ml) was added and the mixture was cooled to 0° C.; the precipitated solid was collected by filtration (10 gm). The mother liquor was concentrated under reduced pressure and the residue was taken in ether (400 ml); a stream of hydrogen chloride gas was bubbled through the solution for 35 min, stirred at room temp. for 0.5 hr. After removal of the solvent, the precipitated solid was collected by filtration and washed thoroughly with ether to give an additional amount of the product. Ethyl (E)-2-(2-thienyl)-2-(hydroxyimino) acetate was obtained as white crystalline solid (38 gm, 92% yield).

Step 2

Ethyl (E)-2-(2-thienyl)-2-[(1,5-dibenzhydryloxy-4-pyridon-2-yl methoxy)imino]acetate A solution of 1,5-dibenzhydryloxy-2-hydroxymethyl-4-pyridone (EP 0251 299) (46.7 gm) in dimethylformamide (200 ml) was gently heated until the solution became clear. After cooling the solution to room temperature, 19.0 gm of ethyl (E)-2-(2-thienyl)-2-(hydroxyimino) acetate and 25.0 gm of triphenyl phosphine was added. To this mixture was added diethyl azodicarboxylate (15 ml) dropwise and the mixture was reacted at room temperature for 2 hours under stirring. DMF was removed under reduced pressure and the residue was taken in ethyl acetate (300 ml), washed successively with water and brine and dried to obtain 40 gm of the above identified compound.

NMR (DMSO-d₆): δ 1.30 (t, 3H), 4.35 (q, 2H), 5.00 (br, s, 2H), 6.00 (s, 1H), 6.35 and 6.40 (2s, 2H), 7.20–7.45 (m, 11H), 7.72 (d, 1H), 7.77 (s, 1H), 7.98 (d, 1H).

Step 3

(E)-2-(2-thienyl)-2-[(1,5-dibenzhydryloxy-4-pyridon-2-yl methoxy)imino]acetic acid A mixture of ethyl (E)-2-(2-thienyl)-2-[(1,5-dibenzhydryloxy-4-pyridon-2-yl methoxy)imino] acetate (from step 2, 17.74 gm) in methanol (350 ml) and THF (75 ml) was stirred at room temperature until the reaction mixture became clear. To this mixture an aqueous solution of NaOH (1.58 gm dissolved in 100 ml of water) was added dropwise over 20 min, and the mixture was stirred at room temp. for 5 hr. After completion of the reaction, solvent was removed under reduced pressure. The residue was diluted with water (350 ml), cooled in an ice-bath and carefully acidified by dropwise addition of dilute hydrochloric acid (3.5 ml of conc. HCl dissolved in 15 ml of water) with vigorous stirring. At pH 2~3, fine white solid started to precipitate out. To the mixture chloroform (500 ml) was added and partitioned. The aqueous layer was separated out and reextracted with $CHCl_3$ (2×200 ml). The combined organic layer was concentrated to dryness. The solid thus obtained was suspended in ether (100 ml), stirred for 30 min, filtered off and washed thoroughly with ether (2×30 ml). The solid was dried over $P_2O_5$ under vacuum to obtain 17.5 gm of the above identified product.

NMR (DMSO-$d_6$): δ 4.96 (br, s, 2H), 6.01 (s, 1H), 6.37 and 6.40 (2s, 2H), 7.20–7.50 (m, 1H), 7.70 (d, 1H), 7.80 (s, 1H), 7.95 (d, 1H).

Step 4

(3S)-trans-3-[(E)-2-(2-thienyl)-2-{(1,5-dibenzhydryloxy-4-pyridon-2-yl methoxy)imino}acetamido]-4-methyl-2-oxoazetidine-1-sulfonic acid, potassium salt A mixture of (3S)-trans-3-amino-4-methyl-2-oxoazetidine-1-sulfonic acid[1.37 gm, *J. Org. Chem.,* 47, 5160, (1982)], (E)-2-(2-thienyl)-2-[(1,5-dibenzhydryloxy-4-pyridon-2-ylmethoxy)imino]acetic acid (step 3, 4.89 gm), DCC (1.73 gm) and 1-hydroxybenzotriazole (1.13 gm) in DMF (50 ml) was stirred under $N_2$ at room temperature for 30 min, $KHCO_3$ (0.762 gm) was added in one portion and the mixture was stirred at room temperature for 24 hr. The solid was filtered off and the filtrate was evaporated under reduced pressure to remove DMF. The crude product was taken in THF (50 ml) and cooled to –30° C. The solid was filtered off and the filtrate was evaporated to dryness. The residue (7.5 gm) was dissolved in 10 ml of methanol and diluted with ether with stirring at room temperature. The separated fine solid was collected by filtration. The filtrate was concentrated again to give a foam which was dissolved in minimum amount of methanol and diluted with ether. The separated solid was collected by filtration and air dried. Total mass of the product was 6.0 gm, which was used for the next step.

Step 5

(3S)-trans-3-[(E)-2-(2-thienyl)-2-{(1,5-dihydroxy-4-pyridon-2-ylmethoxy)imino}acetamido]-4-methyl-2-oxoazetidine-1-sulfonic acid 25.0 gm of (3S)-trans-3-[(E)-2-(2-thienyl)-2-{(5-benzhydryloxy-4-pyridon-2-yl methoxy)imino}acetamido]-4-methyl-2-oxoazetidine-1-sulfonic acid, potassium salt (from Step 4) was taken in 40 ml of dry methylene chloride and anisole mixture (1:1) and cooled to –10° C., trifluoroacetic acid (46 ml) was added dropwise over 10 min, an additional amount of methylene chloride (20 ml) was added and the mixture was stirred at –10° C. for 2 hr. All the volatile solvents were removed under reduced pressure and the residue was digested with ether and the solvent was decanted off. The residue was finally digested with ethyl acetate and the off-white precipitated solid was collected by filtration. The solid thus obtained was crystallized from methanol-water to provide 8.0 gm of the target compound as white powder; m.p. 170° C. (decomp.).

C, H analysis: Calcd, C, 40.67; H, 3.41; N, 11.86 Found, C, 40.14; H, 3.46; N, 11.44

NMR (DMSO-$d_6$): δ 1.41 (d, 3H, J=6.15 Hz), 3.78–3.82 (m, 1H), 4.49 (dd, 1H, J=2.68 Hz and 8.25 Hz), 5.58 (s, 2H), 7.10 (s, 1H), 7.27 (dd, 1H, J=4.0 Hz and 5.0 HZ), 7.82 (dd, 1H, J=1.0 Hz and 4.0 Hz), 8.01 (dd, 1H, J=1.0 Hz and 5.0 Hz), 8.28 (s, 1H), 9.40 (d, J=8.25 Hz).

Preparation of Compound 14

(EXAMPLE 2)

Step 1

Allyl (E)-2-(2-thienyl)-2-[(5-benzhydryloxy-4-pyranon-2-yl methoxy)imino]acetate To an ice cooled solution of allyl (E)-2-(2-thienyl)-2-(hydroxyimino)acetate (1.0 gm, 4.734 mmol), 5-benzhydryloxy-2-(hydroxymethyl) pyran-4-one (1.46 gm, 4.734 mmol) and triphenylphosphine (1.24 gm, 4.734 mmol) in dry THF (30 ml) under nitrogen was added dropwise diethyl azodicarboxylate (820 μl, 5.208 mmol). The reaction mixture was stirred at room temperature overnight and concentrated under reduced pressure to afford the crude as yellow gum (4.93 gm). The product was purified by silica gel column chromatography using hexane-ethyl acetate (2:1) as eluant to provide the title compound as a gummy foam in 47% yield (1.11 gm).

$^1$H NMR (DMSO-$d_6$): δ 8.15 (s, 1H); 8.01 (dd, 1H, J=0.85 Hz and 5.0 Hz); 7.76 (dd, 1H, J=1.0 Hz and 4.0 Hz); 7.23–7.46 (m, 11H); 6.48 (s, 1H); 6.47 (s, 1H); 5.91–6.11 (m, 1H); 5.28–5.43 (m, 2H); 5.25 (s, 2H); 4.84 (d, 2H, J=5.51 Hz).

Step 2

Sodium (E)-2-(2-thienyl)-2-[(5-benzhydryloxy-4-pyranon-2-yl methoxy)imino]acetate A solution of allyl (E)-2-(2-thienyl)-2-[(5-benzhydryloxy-4-pyranon-2-yl methoxy)imino]acetate (from Step 1, Example 2, 2.09 gm, 4.17 mmol), in a mixture of methylene chloride and ethyl acetate (25 ml: 55 ml) was treated with sodium 2-ethylhexanoate (693 mg, 4.17 mmol), triphenylphosphine (109 mg, 0.417 mmol) and Pd $(PPh_3)_4$ (193 mg, 0.167 mmol) and the mixture was stirred at room temperature for 5 hrs. The resulting precipitate was filtered, washed with a mixture of ether-ethyl acetate (1:1) and dried in vacuo to afford a white solid (2.0 gm, 99% yield).

$^1$H NMR (DMSO-$d_6$): δ 8.10 (s, 1H); 7.72 (dd, 1H, J=0.9 Hz and 5.0 Hz); 7.61 (dd, 1H, J=1.0 Hz and 4.0 Hz); 7.24–7.45 (m, 10H); 7.10 (dd, 1H, J=4.0 Hz and 5.0 Hz); 6.47 (s, 1H); 6.34 (s, 1H); 4.96 (s, 2H).

Step 3

(E)-2-(2-Thienyl)-2-[(5-benzhydryloxy-4-pyranon-2-yl methoxy)imino]acetic acid

A suspension of sodium (E)-2-(2-thienyl)-2-[(5-benzhydryloxy-4-pyranon-2-yl methoxy) imino]acetate (from Step 2, Example 2, 1.07 gm, 2.07 mmol) in 30% $NH_4OH$ (25 ml) in a steel bomb was heated at 90° C. for 1 hr. On cooling to room temp. $N_2$ gas was bubbled through and the brown solution was cooled to 0° C. and the pH was carefully adjusted to ~2.0 with 50% HCl. The precipitated solid was filtered off, washed with water, ethyl acetate, hexane and dried successively to give a beige solid in 60% yield (610 mg).

$^1$H NMR (DMSO-$d_6$): δ 7.89 (dd, 1H, J=0.8 and 5.0 Hz); 7.76 (dd, 1H, J=1.0 and 4.0 Hz); 7.69 (s, 1H); 7.16–7.61 (m, 11H); 6.61 (s, 1H); 6.58 (s, 1H); 5.16 (s, 2H).

Step 4

(3S)-trans-3-[(E)-2-(2-thienyl)-2-{5-benzhydryloxy-4pyridon-2-yl methoxy)imino}acetamido]-4-methyl-2-oxoazetidine-1-sulfonic acid, potassium salt A mixture of (3S)-trans-3-amino-4-methyl-2-oxoazetidine-1-sulfonic acid, potassium salt [373 mg, 1.71 mmol, *J. Org. Chem.*, 47, 5160 (1982)], (E)-2-(2-thienyl)-2-[(5-benzhydryloxy-4-pyridon-2-yl methoxy)imino]acetic acid (Step 3, Example 2, 656 mg, 1.425 mmol), DCC (294 mg, 1.425 mmol) and 1-hydroxybenzotriazole (193 mg, 1.425 mmol) in dry DMF (40 ml) was stirred under $N_2$ at room temp. for 20 hrs, filtered and the filtrate was concentrated to dryness under reduced pressure to give a gum which was dissolved in a mixture of acetonitrile-water (7:3) and freeze dried to give a brown fluffy mass (1.21 gm). The product was purified over a HP-20 column using acetonitrile-water as eluant. The appropriate fractions were collected and freeze dried to afford the title compound as a light brown fluff solid in 63% yield (590 mg).

$^1$H NMR (DMSO-$d_6$): δ 9.34 (d, 1H, J=8.3 Hz); 8.12 (s, 1H); 7.97 (dd, 1H, J=1.0 Hz and 5.0 Hz); 7.78 (dd, 1H, J=1.0 Hz and 3.8 Hz); 7.21–7.52 (m, 11H); 7.06 (s, 1H); 6.76 (s, 1H); 5.37 (s, 2H); 4.47 (dd, 1H, J=2.7 Hz and 8.3 Hz); 3.76–3.81 (m, 1H); 1.40 (d, 3H, J=6.14 Hz).

Step 5

(3S)-trans-3-[(E)-2-(2-thienyl)-2{(5-hydroxy-4-pyridon-2-yl methoxy)imino}acetamido]-4-methyl-2-oxoazetidine-1-sulfonic acid, potassium salt A suspension of (3S)-trans-3 -[(E)-2-(2-thienyl)-2-{(5-benzhydryloxy-4-pyridon-2-yl methoxy)imino}acetamido]-4-methyl-2-oxoazetidine-1-sulfonic acid, potassium salt (from Step 4, Example 2, 570 mg, 0.863 mmol) in dry anisole (1 ml) at −10° C. was treated with trifluoroacetic acid (1.33 ml) and stirred for 2 hr. The reaction mixture was concentrated under reduced pressure to give a gum which was triturated with diethyl ether followed by a mixture of ethyl acetate-ether (5:1) to give a light brown solid (440 mg). Purification over a HP-20 column using acetone-water (1:10) as eluant and after freeze-drying of the appropriate fractions, the title compound was obtained as a pale yellow fluffy solid, 226 mg (53% yield).

$^1$H NMR (DMSO-$d_6$): δ 9.36 (br, s, 1H); 7.93 (dd, 1H, J=0.9 Hz and 5.0 Hz); 7.77 (dd, 1H, J=0.9 Hz and 4.0 Hz); 7.53 (br, s, 1H); 7.21 (dd, 1H, J=4.0 Hz and 5.0 Hz); 6.46 (br, s, 1H); 5.20 (s, 2H); 4.49 (s, 1H); 3.81–3.86 (m, 1H); 1.41 (d, 3H, J=6.2 Hz).

TABLE 2

$^1$H NMR spectra of some representative compounds

| Compd No. | Solvent | δ (ppm) |
|---|---|---|
| 3 | $D_2O$ | 7.71–7.79 (m, 2H); 7.56 (s, 1H); 7.15 (s, 1H); 6.60 (s, 1H); 5.37 (s, 2H); 4.54 (d, 1H); 4.23–4.34 (m, 1H); 1.53 (d, 3H, J=6.0 Hz). |
| 4 | DMSO-$d_6$ | 9.32 (d, 1H, J=8.3 Hz); 8.18 (s, 1H); 8.02 (d, 1H, J=4.1 Hz); 7.70–7.80 (m, 1H); 7.26 (t, 1H, J=5.0 Hz); 6.95 (s, 1H); 5.83 (q, 1H, J=7.0 Hz); 4.40–4.48 (m, 1H); 3.70–3.80 (br, m, 1H); 1.66 (d, 3H, J=7.0 Hz); 1.38 (d, 3H, J=5.9 Hz). |
| 5 | DMSO-$d_6$ | 9.33 (br, s, 1H); 7.95 (d, 1H, J=4.7 Hz); 7.78 (t, 1H, J=3.2 Hz); 7.50 (s, 1H); 7.22 (t, 1H, J=4.5 Hz); 6.36 (d, 1H, J=2.0 Hz); 5.75–5.95 (m, 2H); 5.03–5.15 (m, 2H); 4.41 (br, s, 1H); 3.75–3.83 (m, 1H); 2.55–2.85 (m, 2H); 1.37 (d, 3H, J=5.95 Hz). |
| 6 | DMSO-$d_6$ | 9.41 (br, s, 1H); 7.92–7.98 (m, 1H); 7.73–7.80 (m, 1H); 7.40–7.58 (m, 2H); 7.10–7.30 (m, 4H); 6.93 (s, 1H); 6.31 (s, 1H); 4.40–4.48 (m, 1H); 3.75–3.90 (m, 1H); 1.39 (d, 3H, J=6.1 Hz). |
| 7 | DMSO-$d_6$ | 9.35 (d, 1H, J=8.4 Hz); 7.97 (s, 1H); 7.88 (dd, 1H, J=1.0 Hz and 5.0 Hz); 7.80 (dd, 1H, J=1.0 Hz and 4.0 Hz); 7.20 (dd, 1H, J=4.0 Hz and 5.0 Hz); 7.05 (s, 1H); 4.50 (dd, 1H, J=2.6 Hz and 8.2 Hz); 4.46 (t, 2H, J=6.0 Hz); 3.94 (s, 2H); 3.83 (m, 1H); 3.00 (t, 2H, J=6.0 Hz); 1.41 (d, 3H, J=6.0 Hz). |
| 8 | DMSO-$d_6$ | 9.35–9.45 (m, 1H); 7.50–7.95 (m, 3H); 7.12–7.20 (m, 1H); 6.81 (s, 1H); 4.35–4.70 (m, 4H); 4.08–4.20 (m, 1H); 3.79–3.89 (m, 1H); 2.98–3.55 (m, 2H); 1.42 (d, 3H, J=6.1 Hz). |
| 9 | DMSO-$d_6$ | 9.15 (br, s, 1H); 7.79–7.84 (m, 2H); 7.56–7.66 (m, 3H); 7.10–7.15 (m, 2H); 6.96–7.05 (m, 1H); 6.67 (s, 1H); 5.11 (s, 2H); 4.40–4.46 (m, 3H); 3.78–3.84 (m, 1H); 3.60–3.70 (br, m, 2H); 1.40 (d, 3H, J=6.2 Hz). |
| 10 | DMSO-$d_6$ | 8.75 (br, s, 1H); 7.75–7.90 (m, 5H); 7.58 (s, 1H); 7.10–7.18 (m, 2H); 6.52 (s, 1H); 6.33 (s, 2H); 4.36–4.50 (m, 3H); 3.53–3.85 (m, 3H); 1.40 (d, 3H, J=6.0 Hz). |
| 11 | DMSO-$d_6$ | 8.10 (br, s, 1H); 7.96 (d, 1H, J=5.0 Hz); 7.90 (br, s, 1H); 7.74 (d, 1H, J=3.2 Hz); 7.24 (s, 1H); 7.16 (t, 1H, J=5.0 Hz); 6.04 (s, 1H); 5.14 (s, 2H); 4.28–4.52 (m, 3H); 3.89–3.98 (m, 1H); 3.56 (br, s, 2H); 1.96 (s, 3H); 1.41 (d, 3H, J=6.1 Hz). |
| 12 | DMSO-$d_6$ | 9.30 (br, s, 1H); 8.89 (br, t, 1H); 7.84–7.90 (m, 2H); 7.68 (s, 1H); 7.05–7.30 (m, 3H); 6.70 (s, 1H); 6.65 (s, 1H); 5.08 (s, 2H0; 4.40–4.50 (m, 3H); 3.80–3.90 (m, 1H); 3.58–3.70 (m, 2H); 1.41 (d, 3H, J=6.2 Hz). |
| 13 | DMSO-$d_6$ | 9.30 (br, s, 1H); 8.58 (br, s, 1H); 7.83–7.88 (m, 2H); 7.76 (dd, 1H, J=1.0 Hz and 4.0 Hz); 7.38 (s, 1H); 7.15 (dd, 1H, J=4.0 Hz and 5.0 Hz); 4.47 (br, s, 1H); 4.39 (t, 2H, J=5.3 Hz); 3.80–3.84 (m, 1H); 3.55–3.67 (m, 2H); 1.40 (d, 3H, J=6.2 Hz). |
| 15 | DMSO-$d_6$ | 9.28 (br, d, 1H); 7.68 (s, 1H); 6.90 (s, 1H); 6.59–6.66 (m, 2H); 6.10 (dd, 1H, J=1.0 Hz and 2.0 Hz); 5.19 (s, 2H); 4.42 (br, s, 1H); 3.80–3.85 (m, 1H); 3.50 (s, 3H); 1.39 (d, 3H, J=6.0 Hz). |
| 16 | DMSO-$d_6$ | 9.35 (d, 1H, J=8.0 Hz); 7.80–7.93 (m, 4H); 7.16–7.40 (m, 3H); 6.89 (s, 1H); 5.21 (s, 2H); 4.48–4.65 (m, 4H); 4.05–4.12 (m, 1H); 3.74–3.82 (m, 1H); 3.50–3.70 (m, 3H); 1.27 (d, 3H, J=6.1 Hz). |

TABLE 3

ANTIBACTERIAL ACTIVITY OF CEFTADIZIME WITH COMPOUNDS (β-LACTAMASE INHIBITOR)

| | MIC of ceftazidime (μg/ml) | | | | | | |
|---|---|---|---|---|---|---|---|
| Organism | alone | with Ref. Compd. I (Aztreonam) | with Ref. Compd. II | with Ref. Compd. III | with Compd. 1 | with Compd. 2 | with Compd. 3 |
| E. cloacae 40054 | >32 | >32 | 32 | 1.0 | 1.0 | 1.0 | 1.0 |
| E. cloacae MNH-2 | >32 | >32 | >32 | >32 | 2.0 | 4.0 | 2.0 |
| E. cloacae P99 | >32 | >32 | 16 | >32 | >32 | >32 | 32 |
| E. aerogenes S-95 | >32 | 32 | 8.0 | 4.0 | 1.0 | 4.0 | 0.5 |
| E. aerogenes 41006 | >32 | >32 | >32 | >32 | — | >32 | >32 |
| M. morganii 36014 | 32 | — | <0.25 | <0.25 | <0.25 | <0.25 | <0.25 |
| M. morganii 36030 | >32 | <0.25 | <0.25 | <0.25 | <0.25 | <0.25 | <0.25 |
| P. aeruginosa L46004 | >32 | >32 | >32 | >32 | 16 | 32 | 32 |
| P. aeruginosa 46012 (R) | >32 | >32 | >32 | 32 | 4.0 | 16 | 8.0 |
| P. aeruginosa 46017 | >32 | >32 | >32 | 32 | 4.0 | 16 | 4.0 |
| P. aeruginosa 46220 DR-2 | 32 | 8.0 | 16 | <0.25 | <0.25 | <0.25 | 1.0 |
| P. aeruginosa 46220 DR-2-1 | >32 | >32 | >32 | 16 | <0.25 | 1.0 | 2.0 |
| P. aeruginosa CT-122 | 32 | 16 | 16 | 8.0 | 4.0 | 8.0 | 8.0 |
| P. aeruginosa CT-137 | 16 | 16 | 32 | 4.0 | 2.0 | 4.0 | 4.0 |
| P. aeruginosa CT-144 | >32 | >32 | >32 | 8.0 | 1.0 | 2.0 | 4.0 |
| P. aeruginosa PAO 303 carb-4 | 32 | 32 | 32 | 4.0 | 4.0 | 4.0 | 2.0 |
| P. aeruginosa sp 2439 Wt. | >32 | >32 | >32 | 32 | 4.0 | 8.0 | 4.0 |
| P. fluorescens sp 5953 | >32 | >32 | >32 | >32 | 4.0 | 8.0 | 8.0 |
| P. aeruginosa M 1405 | >32 | >32 | >32 | 32 | 2.0 | 8.0 | 32 |
| P. aeruginosa M 2297 | >32 | >32 | >32 | 32 | 32 | 16 | 32 |
| P. aeruginosa AU-1 | >32 | >32 | — | 16 | 4.0 | 8.0 | 8.0 |
| P. aeruginosa AU-5 | >32 | <0.25 | — | 8.0 | 2.0 | 2.0 | 8.0 |
| P. aeruginosa AU-7 | >32 | >32 | — | 16 | 4.0 | 8.0 | 8.0 |
| P. aeruginosa AU-8 | >32 | >32 | — | — | 8.0 | 8.0 | 8.0 |
| P. aeruginosa AU-10 | 32 | 16 | — | 8.0 | 4.0 | 4.0 | 4.0 |

| | MIC of ceftazidime (μg/ml) | | | | | |
|---|---|---|---|---|---|---|
| Organism | alone | with Ref. Compd. I (Aztreonam) | with Compd. 7 | with Compd. 8 | with Compd. 9 | with Compd. 10 |
| E. cloacae 40054 | >32 | >32 | <0.25 | 0.5 | 1.0 | <0.25 |
| E. cloacae MNH-2 | >32 | >32 | >32 | >32 | 8.0 | 8.0 |
| E. cloacae P 99 | >32 | >32 | 32 | >32 | >32 | >32 |
| E. aerogenes S-95 | >32 | 32 | 1.0 | 0.5 | 1.0 | 1.0 |
| E. aerogenes 41006 | >32 | >32 | 32 | >32 | — | — |
| M. morganii 36014 | 32 | — | — | — | — | — |
| M. morganii 36030 | >32 | <0.25 | <0.25 | 2.0 | 2.0 | <0.25 |
| P. aeruginosa L 46004 | >32 | >32 | 8.0 | 16 | 8.0 | 32 |
| P. aeruginosa 46012 (R) | >32 | >32 | 8.0 | 32 | 1.0 | 1.0 |
| P. aeruginosa 46017 | >32 | >32 | 8.0 | 32 | 1.0 | 0.5 |
| P. aeruginosa 46220 DR-2 | 32 | 8.0 | 1.0 | 1.0 | 0.5 | 0.5 |
| P. aeruginosa 46220 DR-2-1 | >32 | >32 | 0.5 | 2.0 | <0.25 | <0.25 |
| P. aeruginosa CT-122 | 32 | 16 | 4.0 | 8.0 | 2.0 | 2.0 |
| P. aeruginosa CT-137 | 16 | 16 | 2.0 | 2.0 | 1.0 | 1.0 |
| P. aeruginosa CT-144 | >32 | >32 | 2.0 | 8.0 | 0.5 | 1.0 |
| P. aeruginosa PAO 303 carb-4 | 32 | 32 | 2.0 | — | 2.0 | 2.0 |
| P. aeruginosa sp 2439 Wt. | >32 | >32 | 2.0 | 8.0 | 2.0 | 4.0 |
| P. fluorescens sp 5953 | >32 | >32 | 8.0 | 8.0 | 1.0 | 1.0 |
| P. aeruginosa M 1405 | >32 | >32 | 8.0 | 16 | 0.5 | 1.0 |
| P. aeruginosa M 2297 | >32 | >32 | 8.0 | 32 | 32 | 32 |
| P. aeruginosa AU-1 | >32 | >32 | 8.0 | 8.0 | 2.0 | 4.0 |
| P. aeruginosa AU-5 | >32 | <0.25 | — | — | 1.0 | 2.0 |
| P. aeruginosa AU-7 | >32 | >32 | 8.0 | 8.0 | 2.0 | 4.0 |
| P. aeruginosa AU-8 | >32 | >32 | 8.0 | 8.0 | 8.0 | 8.0 |
| P. aeruginosa AU-10 | 32 | 16 | 4.0 | 8.0 | 2.0 | 2.0 |

We claim:

1. A compound of formula (I)

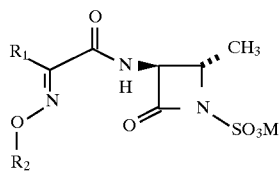

wherein $R_1$ is selected from the group consisting of 2-thienyl, 2-furyl, 2-pyrrolyl, 1-methyl-2-pyrrolyl, 2-amino-1-thiazolyl and 5-isothiazolyl;

$R_2$ is selected from the group consisting of:

(a) 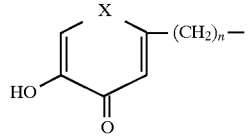

wherein n = 1 or 2, and X = NH, N—OH or pharmaceutically acceptable salts thereof;

(b) 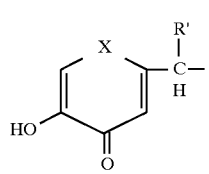

wherein X = NH, N—OH or pharmaceutically acceptable salts thereof, R' = (C1–6) alkyl, allyl, phenyl unsubstituted or substituted with fluorine (c) 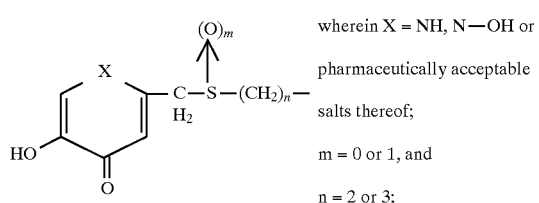

wherein X = NH, N—OH or pharmaceutically acceptable salts thereof; m = 0 or 1, and n = 2 or 3;

(d) 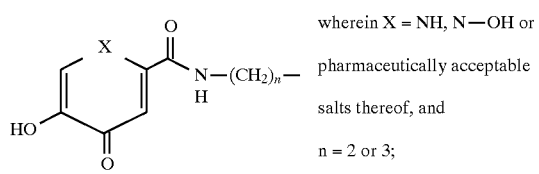

wherein X = NH, N—OH or pharmaceutically acceptable salts thereof, and n = 2 or 3;

(e) 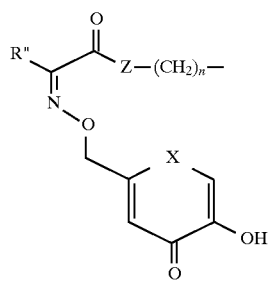

wherein R" = CH3, n = 2 or 3; Z = NH or O wherein X = NH, N—OH or pharmaceutically acceptable salts thereof;

(f) 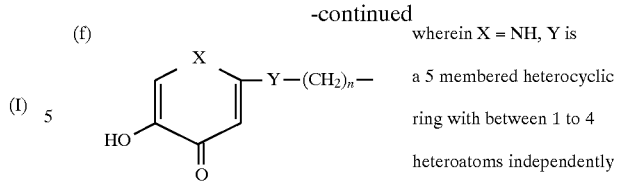

wherein X = NH, Y is a 5 membered heterocyclic ring with between 1 to 4 heteroatoms independently selected from O, S and N, and n is 1, 2, 3, or 4

(g) 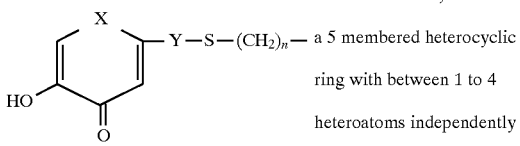

wherein X = NH, Y is a 5 membered heterocyclic ring with between 1 to 4 heteroatoms independently selected from O, S and N, and n is 1, 2, 3, or 4;

M is hydrogen or a pharmaceutically acceptable cation; wherein the oxyimino fragment (=N—OR$_2$) in formula (I) is in the 'anti' orientation.

2. The compound according to claim 1 where the $R_1$ is selected from the group consisting of 2-thienyl and 2-amino-4-thiazolyl.

3. The compound according to claim 2, wherein $R_1$ is 2-thienyl.

4. The compound according to claim 1 where $R_2$ is hydroxypyridone and its derivatives as represented by the following formula:

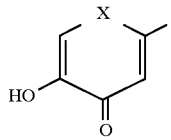

where X = NH and N—OH or pharmaceutically acceptable salts thereof.

5. The compound according to claim 4, wherein when X is N—OH, $R_2$ is a keto or enol tautomeric isomer of the formula:

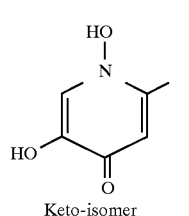 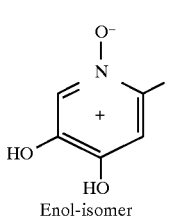

Keto-isomer    Enol-isomer

6. The method for inhibiting β-lactamase-mediated inactivation of a β-lactam antibiotic, which comprises administering to a patient an effective amount of the compound described in claim 1 or a pharmaceutically acceptable salt thereof.

7. The compound according to claim 1, wherein Y is selected from the group consisting of

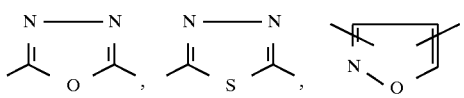

-continued

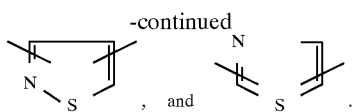

8. The compound according to claim 1, wherein said compound contains variable amounts of water.

9. The compound according to claim 8, wherein said variable amounts of water result from lyophilization, crystallization or column purification.

10. A pharmaceutical composition suitable for the treatment of bacterial infections in mammals comprising the compound described in claim 1 or a pharmaceutically acceptable salt thereof and a pharmaceutically acceptable carrier.

11. A β-lactamase inhibitor for a β-lactam antibiotic, which comprises as an active ingredient the compound described in claim 1 or a pharmaceutically acceptable salt thereof in combination with a pharmaceutically acceptable carrier.

* * * * *

UNITED STATES PATENT AND TRADEMARK OFFICE
CERTIFICATE OF CORRECTION

PATENT NO. : 5,888,998

DATED : March 30, 1999

INVENTOR(S) : MAITI et al.

It is certified that error appears in the above-identified patent and that said Letters Patent is hereby corrected as shown below:

Column 1, line 32, delete "of" insert therefor -- and --

Column 3, 63, delete "ceftizoxime," insert therefor -- cefuroxime, --

Column 8, line 28, delete "Exemlplary" insert therefor -- Exemplary --

Column 21, lines 31 and 51, delete "2-ylmethoxy)" insert therefor -- 2-yl methoxy) --

Column 22, line 3, delete "(d, 3H, J==6.15 Hz)" insert therefor -- (d, 3H, J=6.15 Hz) --

Column 22, line 5, delete "(dd, 1H, J=4.0 Hz and 5.0 HZ)" insert therefor -- (dd, 1H, J=4.0 Hz and 5.0 Hz) --

Table 2, Compd. No. 10, delete "6.33" insert therefor -- 5.33 --

Table 2, Compd. No. 12, line 2, delete "(s, 2HO;" insert therefor -- (s, 2H); --

Item [57], $R_1$: delete "2-amino-1-thiazolyl" insert therefor -- 2-amino-4-thiazolyl --

Column 27, line 17, $R_1$: delete "2-amino-1-thiazolyl" insert therefor -- 2-amino-4-thiazolyl --

UNITED STATES PATENT AND TRADEMARK OFFICE
CERTIFICATE OF CORRECTION

PATENT NO. : 5,888,998

DATED : March 30, 1999

INVENTOR(S) : Maiti et al.

It is certified that error appears in the above-indentified patent and that said Letters Patent is hereby corrected as shown below:

Table 1, delete "Compound 9" insert therefor --

TABLE 1-continued

| Compound | $R_1$ | $R_2$/orientation of $OR_2$ | M | $IC_{50}$, μM |
|---|---|---|---|---|
| 9 | (thiophene) | (structure with thiophene, amide, anti, OH, N-O, pyridinone-OH) | K | 0.006 |

--

Signed and Sealed this

Tenth Day of April, 2001

Attest:

NICHOLAS P. GODICI

Attesting Officer    Acting Director of the United States Patent and Trademark Office